United States Patent
Vandenbossche et al.

(10) Patent No.: US 6,673,122 B1
(45) Date of Patent: Jan. 6, 2004

(54) COMPOSITIONS FOR DYEING KERATIN FIBERS CONTAINING PARA-AMINOPHENOLS, DYEING PROCESS, NOVEL PARA-AMINOPHENOLS AND PROCESS FOR THEIR PREPARATION

(75) Inventors: Jean Jacques Vandenbossche, Sevran (FR); Alain Lagrange, Coupvray (FR)

(73) Assignee: L'Oréal, Paris (FR)

( * ) Notice: Subject to any disclaimer, the term of this patent is extended or adjusted under 35 U.S.C. 154(b) by 0 days.

(21) Appl. No.: 09/694,823

(22) Filed: Oct. 24, 2000

Related U.S. Application Data

(63) Continuation of application No. 09/028,674, filed on Feb. 24, 1998.

(30) Foreign Application Priority Data

Feb. 26, 1997 (FR) .............................. 97 02307

(51) Int. Cl.[7] ................................. A61K 7/13
(52) U.S. Cl. ............. 8/405; 8/408; 8/409; 8/410; 8/412; 8/421; 8/423; 8/570
(58) Field of Search ................ 8/409, 408, 412, 8/405, 410, 421, 423, 570

(56) References Cited

U.S. PATENT DOCUMENTS

| | | | |
|---|---|---|---|
| 4,013,404 A | 3/1977 | Parent et al. ................... | 8/423 |
| 4,189,433 A | 2/1980 | Ohnsorge et al. ............ | 548/207 |
| 4,248,788 A | 2/1981 | Bourgery et al. ......... | 260/340.3 |
| 4,322,212 A | 3/1982 | Konrad et al. ................ | 8/409 |
| 4,395,262 A | 7/1983 | Konrad et al. ................ | 8/423 |
| 4,517,005 A | 5/1985 | Kolc et al. ...................... | 71/28 |
| 4,776,857 A | 10/1988 | Carroll et al. ................. | 8/409 |
| 4,865,617 A | 9/1989 | Junino et al. .................. | 8/423 |
| 5,053,053 A | 10/1991 | DeLabbey et al. ............ | 8/423 |
| 5,190,564 A | 3/1993 | Lang et al. .................... | 8/423 |
| 5,254,135 A | 10/1993 | Lang et al. .................... | 8/423 |
| 5,494,490 A | 2/1996 | Audousset et al. ........... | 8/409 |
| 5,496,543 A | 3/1996 | Lagrange et al. .......... | 424/70.7 |
| 5,518,506 A * | 5/1996 | Cotteret et al. ............... | 8/409 |
| 5,536,843 A | 7/1996 | Knuebel et al. ............ | 548/469 |
| 5,538,517 A | 7/1996 | Samain et al. ................ | 8/423 |
| 5,578,087 A | 11/1996 | Audousset et al. ........... | 8/423 |
| 5,583,234 A | 12/1996 | Lagrange et al. .......... | 548/455 |
| 5,609,649 A | 3/1997 | Junino et al. .................. | 8/409 |
| 5,620,484 A * | 4/1997 | Maubru et al. ................ | 8/409 |
| 5,645,609 A | 7/1997 | Andrean et al. ............... | 8/423 |
| 5,690,697 A | 11/1997 | Samain ........................... | 8/423 |
| 5,704,948 A | 1/1998 | Terranova et al. ............ | 8/469 |
| 5,752,982 A | 5/1998 | Lang et al. ..................... | 8/423 |
| 5,755,829 A | 5/1998 | Terranova et al. ............ | 8/574 |
| 5,769,903 A | 6/1998 | Audousset et al. ........... | 8/576 |
| 5,785,717 A | 7/1998 | Maubru et al. ................ | 8/576 |
| 5,900,028 A * | 5/1999 | Audousset et al. ........... | 8/409 |
| 5,984,975 A * | 11/1999 | Langrang et al. ............. | 8/412 |
| 6,093,220 A * | 7/2000 | Adousset et al. ............. | 8/412 |

FOREIGN PATENT DOCUMENTS

| | | |
|---|---|---|
| DE | 1492166 | 12/1969 |
| DE | 2527791 | 6/1975 |
| DE | 27 04 793 | 7/1978 |
| DE | 28 16 785 | 10/1978 |
| DE | 2719424 | 11/1978 |
| EP | 30680 | 6/1918 |
| EP | 4366 | 10/1979 |
| FR | 0 428 441 | 5/1991 |
| JP | 63-216861 | 9/1988 |
| SU | 545643 | 2/1977 |
| WO | WO 92 17157 | 10/1992 |

OTHER PUBLICATIONS

G. Menichi et al., No. 416—Recherches 1,18 sur le benzofuranne., "Possibilité d'accés aux furobenzoxazoles par l'intermédiaire d'arylbenzofurannes ortho hydroxyls," Bulletin De la Societe Chimique de France, No. 7–8, 1973, Paris FR, pp. 2352–2354, XP002045612, examples 3,29.

Chemical Abstracts, vol. 79, No. 19, Nov. 12, 1973, Abstract No. 115501.

Chemical Abstracts, vol. 103, No. 25, Dec. 23, 1985, Abstract No. 208461.

Chemical Abstracts, vol. 82, No. 7, Feb. 17, 1975, Abstract No. 38688.

CAS printout, RN 274–09–9 No date.

Erkog et al., "Metabolism of Trifluralin in Rats," J. Agric. Food Chem, pp. 1061–1069.

Katritzky et al., "Synthesis of 4_amino–7–Hydroxybenzimidazole," Heterocycles, vol. 38, No. 11, pp. 2415–2422.

* cited by examiner

Primary Examiner—Yogendra N. Gupta
Assistant Examiner—Eisa Elhilo
(74) Attorney, Agent, or Firm—Finnegan, Henderson, Farabow, Garrett & Dunner LLP

(57) ABSTRACT

Compositions for the oxidation dyeing of keratin fibers, comprising, as oxidation base, at least one para-aminophenol, of formula (I) and/or at least one acid-addition salt thereof:

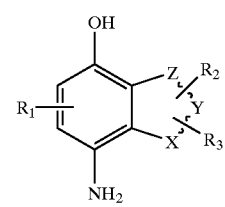

(I)

in which:

$R_1$ represents a hydrogen atom, a linear or branched $C_1$–$C_4$ alkyl radical or a $C_1$–$C_4$ trifluoroalkyl radical, $R_2$ and $R_3$ independently represent a hydrogen atom, a $C_1$–$C_4$ alkyl radical or a $C_1$–$C_4$ monohydroxyalkyl radical, and X, Y and Z independently represent a carbon, nitrogen, oxygen or sulphur atom, wherein the bonds XY and YZ are single or double bonds;

a dyeing process using these compositions, novel para-aminophenols and a process for their preparation.

34 Claims, No Drawings

COMPOSITIONS FOR DYEING KERATIN FIBERS CONTAINING PARA-AMINOPHENOLS, DYEING PROCESS, NOVEL PARA-AMINOPHENOLS AND PROCESS FOR THEIR PREPARATION

This is a continuation of application Ser. No. 09/028,674, filed Feb. 24, 1998, which is incorporated herein by reference.

The invention relates to novel compositions for the oxidation dyeing of keratin fibers, comprising at least one para-aminophenol as oxidation base, to the dyeing process using this composition, to novel para-aminophenols and to a process for their preparation.

It is known to dye keratin fibers, and in particular human hair, with dye compositions containing oxidation dye precursors, in particular ortho- or para-phenylenediamines, ortho- or para-aminophenols and heterocyclic compounds such as diaminopyrazole derivatives, which are generally referred to as oxidation bases. The oxidation dye precursors, or oxidation bases, are colorless or weakly colored compounds which, when combined with oxidizing products, may give rise to colored compounds and dyes by a process of oxidative condensation.

It is also known that the shades obtained with these oxidation bases may be varied by combining them with couplers or coloration modifiers, the latter being selected in particular from aromatic meta-diamines, meta-aminophenols, meta-diphenols and certain heterocyclic compounds.

The variety of molecules used as oxidation bases and couplers makes it possible to obtain a wide range of colors.

The so-called "permanent" coloration obtained by means of these oxidation dyes must moreover satisfy a certain number of requirements. Thus, it must have no toxicological drawbacks and it must allow shades of the desired intensity to be obtained and have good resistance to external agents (light, bad weather, washing, permanent-waving, perspiration and rubbing).

The dyes must also allow white hairs to be covered and, lastly, they must be as unselective as possible, that is to say that they must allow the smallest possible differences in coloration to be produced over the entire length of the same keratin fiber, which may indeed be differently sensitized (i.e. damaged) between its tip and its root.

The inventors have now discovered, entirely surprisingly and unexpectedly, that certain para-aminophenols of formula (I) defined below, for those which are novel per se, are suitable for use as oxidation dye precursors.

This discovery forms the basis of the present invention.

A first subject of the invention is thus a composition for the oxidation dyeing of keratin fibers, and in particular human keratin fibers such as the hair, characterized in that it comprises, in a medium which is suitable for dyeing, as oxidation base, at least one para-aminophenol of formula (I) below, and/or at least one acid-addition salt thereof:

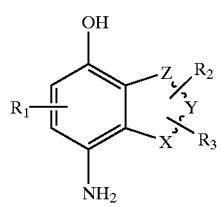

(I)

in which:

$R_1$ represents a hydrogen atom, a linear or branched $C_1$–$C_4$ alkyl radical or a $C_1$–$C_4$ trifluoroalkyl radical, $R_2$ and $R_3$ independently represent a hydrogen atom, a $C_1$–$C_4$ alkyl radical or a $C_1$–$C_4$ monohydroxyalkyl radical, X, Y and Z independently represent a carbon, nitrogen, oxygen or sulphur atom, the bonds XY and YZ can be single or double bonds.

As mentioned above, the oxidation dye compositions in accordance with the invention can produce a coloration on keratin fibers in oxidizing medium.

Another subject of the invention is the use of the para-aminophenols of formula (I) as oxidation base in compositions for the oxidation dyeing of keratin fibers, and in particular human keratin fibers such as the hair.

In general, the acid-addition salts which can be used in the context of the dye compositions of the invention (oxidation bases and couplers) are selected in particular from the hydrochlorides, hydrobromides, sulphates, tartrates, lactates and acetates.

Among the para-aminophenols of formula (I) which can be used as oxidation bases in the compositions in accordance with the invention, mention may be made in particular of:

4-amino-2,2-dimethyl-2,3-dihydrobenzofuran-7-ol,
7-amino-3H-benzoimidazol-4-ol,
7-aminobenzothiophen-4-ol,
7-amino-2,3-dimethylbenzofuran-4-ol,
4-amino-2,3-dimethylbenzofuran-7-ol,
7-amino-1-propyl-5-trifluoromethyl-1H-benzoimidazol-4-ol,
7-aminobenzoisothiazol-4-ol,
7-amino-1H-benzotriazol-4-ol,
4-amino-2,3-dihydro-1H-indol-7-ol,
7-aminoindan-4-ol,
7-amino-5-methyl-2,1,3-benzothiadiazol-4-ol,
7-amino-2,1,3-benzothiadiazol-4-ol,
7-amino-1-methyl-1H-indol-4-ol,
7-amino-1-(2-hydroxyethyl)-1H-indol-4-ol, and the acid-addition salts thereof.

Among these para-aminophenols, the ones more particularly preferred are:

4-amino-2,2-dimethyl-2,3-dihydrobenzofuran-7-ol,
7-amino-3H-benzoimidazol-4-ol,
7-amino-1-methyl-1H-indol-4-ol, and the acid-addition salts thereof.

The para-aminophenol(s) of formula (I) above preferably represent(s) from approximately 0.0005 to approximately 12% by weight relative to the total weight of the dye composition, and even more preferably from approximately 0.005 to approximately 6% by weight.

The medium which is suitable for dyeing (or the support) generally comprises water or a mixture of water and at least one organic solvent to solubilize the compounds which would not be sufficiently soluble in water. Organic solvents which may be mentioned, for example, are $C_1$–$C_4$ lower alkanols such as ethanol and isopropanol; glycerol; glycols and glycol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, similar products and mixtures thereof.

The solvents may be present in proportions preferably ranging from approximately 1 to approximately 40% by weight relative to the total weight of the dye composition, and even more preferably from approximately 5 to approximately 30% by weight, relative to the total weight of the dye composition.

The pH of the dye composition in accordance with the invention preferably ranges from 3 to 12 and more preferably from 5 to 11. It may be adjusted to the desired value using acidifying or basifying agents usually used in the dyeing of keratin fibers.

Among the acidifying agents which may be mentioned, by way of example, are inorganic or organic acids such as hydrochloric acid, orthophosphoric acid, sulphuric acid, carboxylic acids such as acetic acid, tartaric acid, citric acid and lactic acid, and sulphonic acids.

Among the basifying agents which may be mentioned, by way of example, are aqueous ammonia, alkaline carbonates, alkanolamines such as mono-, di- and triethanolamines and derivatives thereof, sodium hydroxide or potassium hydroxide and the compounds of formula (II) below:

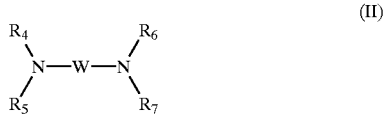

(II)

in which:
W is a propylene residue optionally substituted with a hydroxyl group or a $C_1$–$C_4$ alkyl radical;
$R_4$, $R_5$, $R_6$ and $R_7$ independently represent a hydrogen atom or a $C_1$–$C_4$ alkyl or $C_1$–$C_4$ hydroxyalkyl radical.

In addition to the dyes of formula (I) defined above, the dye composition in accordance with the invention can also contain at least one additional oxidation base which can be selected from the oxidation bases conventionally used in oxidation dyeing and among which mention may be made in particular of para-phenylenediamines, bis(phenyl) alkylenediamines, para-aminophenols, ortho-aminophenols and heterocyclic bases other than the para-aminophenols of formula (I) used in accordance with the invention.

Among the para-phenylenediamines, mention may be made more particularly, by way of example, of para-phenylenediamine, para-toluylenediamine, 2,6-dimethyl-para-phenylenediamine, 2-βhydroxyethyl-para-phenylenediamine, 2-n-propyl-para-phenylenediamine, 2-isopropyl-para-phenylenediamine, N-(β-hydroxypropyl)-para-phenylenediamine, N,N-bis-(β-hydroxyethyl)-para-phenylenediamine, 4-amino-N-(β-methoxyethyl)aniline, and the para-phenylenediamines described in French patent application FR-A-2,630,438, the disclosure of which is specifically incorporated by reference herein, and the acid-addition salts thereof.

Among the bis(phenyl)alkylenediamines, mention may be made more particularly, by way of example, of N,N'bis(β, hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis-(4-aminophenyl) tetramethylenediamine, N,N'-bis-(β-hydroxyethyl)-N,N'-bis(4-aminophenyl)-tetramethylenediamine, N,N'-bis(4-methylaminophenyl)tetramethyiened amine and N,N'-bis (ethyl)-N,N'-bis(4'-amino-3'-methylphenyl) ethylenediamine, and the acid-addition salts thereof.

Among the para-aminophenols, mention may be made more particularly, by way of example of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the acid-addition salts thereof.

Among the ortho-aminophenols, mention may be made more particularly, by way of example, of 2-aminophenol, 2-amino-5-methylphenol, 2-amino-6-methylphenol and 5-acetamido-2-aminophenol, and the acid-addition salts thereof.

Among the heterocyclic bases, mention may be made more particularly, by way of example, of pyridine derivatives, pyrimidine derivatives and pyrazole derivatives, and the acid-addition salts thereof.

When they are used, these additional oxidation bases preferably represent from approximately 0.0005 to approximately 12% by weight relative to the total weight of the dye composition, and even more preferably from approximately 0.005 to approximately 6% by weight relative.

The oxidation dye compositions in accordance with the invention can also contain at least one coupler and/or at least one direct dye, in particular in order to modify the shades or to enrich them with glints.

The couplers which can be used in the oxidation dye compositions in accordance with the invention can be selected from the couplers used conventionally in oxidation dyeing and among which mention may be made in particular of meta-phenylenediamines, meta-aminophenols, meta-diphenols and heterocyclic couplers such as, for example, indole derivatives, indoline derivatives, pyridine derivatives and pyrazolones, and the acid-addition salts thereof.

These couplers are more particularly selected from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy) benzene, 2-amino-4-(>hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one and 1-phenyl-3-methylpyrazol-5-one, and the acid-addition salts thereof.

When they are present, these couplers preferably represent from approximately 0.0001 to approximately 10%, by weight relative to the total weight of the dye composition, and even more preferably from approximately 0.005 to approximately 5% by weight.

The dye composition according to the invention can also contain various adjuvants used conventionally in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, conditioners such as, for example, silicones, film-forming agents, preserving agents and opacifying agents.

Needless to say, a person skilled in the art will take care to select the optional complementary compound(s) mentioned above such that the advantageous properties intrinsically associated with the oxidation dye composition in accordance with the invention are not, or are not substantially, adversely affected by the addition or additions envisaged.

The dye composition according to the invention may be in various forms, such as in the form of liquids, creams, gels or any other form which is suitable for dyeing keratin fibers, and in particular human hair.

A subject of the invention is also a process for dyeing keratin fibers, and in particular human keratin fibers such as the hair, using the dye composition as defined above.

According to this process, at least one dye composition as defined above is applied to the fibers, the color being developed at acidic, neutral or alkaline pH using an oxidizing agent which is added to the dye composition only at the time of use, or which is present in an oxidizing composition that is applied simultaneously or sequentially in a separate manner.

According to a preferred embodiment of the dyeing process according to the invention, the dye composition described above is preferably mixed, at the time of use, with an oxidizing composition containing, in a medium which is suitable for dyeing, at least one oxidizing agent present in an amount which is sufficient to develop a coloration. The mixture obtained is then applied to the keratin fibers and is preferably left in place for approximately 3 to approximately 50 minutes, more preferably approximately 5 to approximately 30 minutes, after which the fibers are rinsed, washed with shampoo, rinsed again and dried.

The oxidizing agent present in the oxidizing composition as defined above may be selected from the oxidizing agents conventionally used for the oxidation dyeing of keratin fibers, and among which mention may be made of hydrogen peroxide, urea peroxide, alkali metal bromates and persalts such as perborates and persulphates. Hydrogen peroxide is particularly preferred.

The pH of the oxidizing composition containing the oxidizing agent as defined above is such that, after mixing with the dye composition, the pH of the resulting composition applied to the keratin.fibers preferably varies from 3 to 12 and even more preferably from 5 to 11. It is adjusted to the desired value using acidifying or basifying agents usually used in the dyeing of keratin fibers and as are defined above.

The oxidizing composition as defined above can also contain various adjuvants used conventionally in compositions for dyeing the hair and as are defined above.

The composition which is finally applied to the keratin fibers may be in various forms, such as in the form of liquids, creams, gels or any other form which is suitable for dyeing keratin fibers, and in particular human hair.

Another subject of the invention is a multi-compartment device or dyeing "kit" or any other multi-compartment packaging system, a first compartment of which contains the dye composition as defined above and a second compartment of which contains the oxidizing composition as defined above. These devices may be equipped with a means which makes it possible to deliver the desired mixture onto the hair, such as the devices described in French patent FR-2,586,913, the disclosure of which is specifically incorporated by reference herein.

Certain para-aminophenols of formula (I) used as oxidation bases in the context of the present invention are novel and, in this respect, constitute another subject of the invention.

These novel para-aminophenols are:

4-amino-2,2-dimethyl-2,3-dihydrobenzofuran-7-ol, 7-amino-1-methyl-1H-indol-4-ol, and the acid-addition salts thereof.

The para-aminophenols of formula (I) in accordance with the invention can be prepared, for example, according to the general process corresponding to the following synthetic scheme:

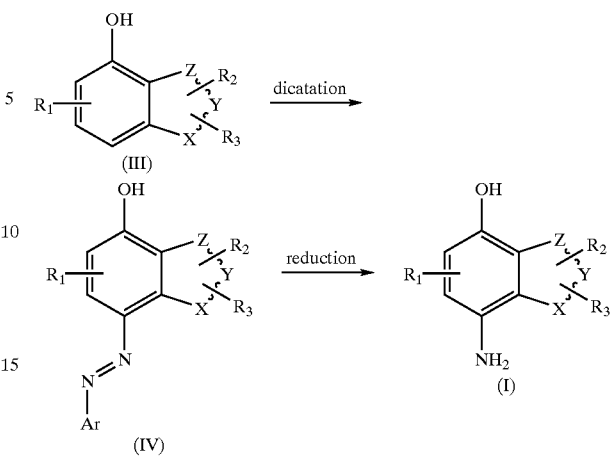

which includes, in a first step, in basifying an aqueous solution of a phenol of formula (III) in which the radicals $R_1$, $R_2$ and $R_3$ and the atoms X, Y and Z have the same meanings as those given above for formula (I), using a strong base, at a temperature preferably ranging from −15° C. to 20° C. and more preferably from −5° C. to 5° C., in order to obtain an aqueous solution of the corresponding phenate, and then, in a second step, in reacting the phenate obtained in the first step with a diazonium salt of an aromatic amine while maintaining the temperature of the medium at a temperature preferably ranging from −15° C. to 20° C. and more preferably from −5° C. to 5° C., in order to obtain the corresponding diazonium compound of formula (IV) in which the radicals $R_1$, $R_2$ and $R_3$ and the atoms X, Y and Z have the same meanings as those given above for formula (I), and then, in a third step, in reducing the diazonium compound of formula (IV), either by chemical reduction or by reduction by catalytic hydrogenation in the presence of an oxidation catalyst and hydrogen or in the presence of a hydrogen donor, in order to obtain the corresponding para-aminophenol of formula (I).

The basifying agent used in the first step is preferably selected from strong bases such as sodium hydroxide and potassium hydroxide.

The aromatic amine used in the second step is preferably selected from anilines that are unsubstituted or mono- or polysubstituted with a $C_1$–$C_4$ alkyl, $C_1$–$C_4$ alkoxy, $C_1$–$C_4$ dialkylamino, nitro, carboxyl or sulphonyl radical.

It is most particularly preferred to use aniline or sulphanilic acid as aromatic amine.

The diazonium salt of the aromatic amine used in the second step is preferably prepared by dissolving the aromatic amine in a solution of strong acid such as, for example, hydrochloric acid, to which a solution of sodium nitrite is then added while maintaining the temperature of the medium at a temperature ranging from −15° C. to 20° C. and more preferably from −5° C. to 5° C.

When the reduction of the compound of formula (IV) is carried out by chemical reduction, dithionite, iron in acetic medium or zinc in alcoholic medium is preferably used as reducing agent.

When the reduction of the compound of formula (IV) is carried out by catalytic hydrogenation, the hydrogen used according to the process of the invention is preferably molecular hydrogen under low pressure.

Among the hydrogen donors, mention may be made of formic acid and olefinic hydrogen donors such as, for example, cyclohexene, substituted cyclohexenes, 1,3-cyclohexadiene and 1,4-cyclohexadiene.

As hydrogenation catalyst, mention may be made, for example, of metals selected from chromium, molybdenum, tungsten, platinum, palladium, rhodium. cobalt, nickel and ruthenium, oxides thereof and combinations of these substances such as, for example, a mixture of cobalt oxide and molybdenum oxide including cobalt molybdate.

The preferred hydrogenation catalysts are palladium or Raney nickel, as well as other platinum-group metals. In a known manner, the catalyst can be deposited on an inert support of neutral pH so as not to influence the pH of the reaction solvent medium. Among these inert supports, mention may be made, for example, of neutral wood charcoal, neutral charcoal, neutral alumina, zeolites, clays, etc. Neutral charcoal is preferably used.

The hydrogenation catalysts are generally present in an amount ranging from 0.2 to 5% by weight of metal equivalent relative to the weight of the compound of formula (IV) to be reacted.

When the reaction is complete, the para-aminophenols of formula (I) in accordance with the invention can, where appropriate, be recovered by methods well known to those skilled in the art, such as crystallization, distillation or vapour-entrainment.

The examples which follow are intended to illustrate the invention without, however, limiting the scope thereof.

PREPARATION EXAMPLE

Preparation Example 1

Synthesis of 4-Amino-2,2-dimethyl-2,3-dihydrobenzofuran-7-ol

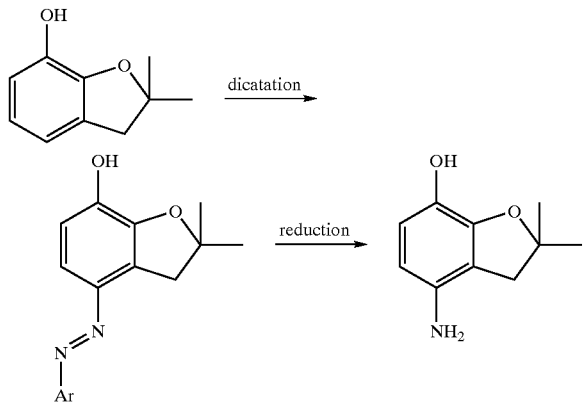

a) Preparation of 2,2-Dimethyl-4-phenylazo-2,3-dihydrobenzofuran-7-ol 56 grams of aniline (0.6 mol) were dissolved in a mixture of 800 ml of water and ice acidified with 130 ml of 12N hydrochloric acid. 100 ml of an aqueous solution of 46 g of sodium nitrite (0.66 mol) were then run into this mixture over 10 minutes, while maintaining the reaction temperature at 0° C.

The pale yellow solution thus obtained was maintained at 0° C. and run, over one hour with stirring, into a solution which had been obtained by dissolving 98.4 g of phenol (0.6 mol) in a mixture of 1500 ml of water and ice basified with 90 ml of 10N sodium hydroxide over 30 minutes and at 0° C.

An orange precipitate was obtained, which was filtered, washed with water and then dried in order to obtain 154 g of the desired azo compound. The product obtained was then recrystallized from cyclohexane to give orange crystals whose melting point was 98° C. The elemental analysis calculated for $C_{16}H_{16}N_2O_2$ was:

| % | C | H | N | Cl |
|---|---|---|---|---|
| Calculated | 71.62 | 6.01 | 10.44 | 11.93 |
| Found | 71.69 | 6.12 | 10.18 | 11.43 | b) Preparation of 4-Amino-2,2-dimethyl-2,3-dihydrobenzofuran-7-ol 134 g (0.5 mol) of the azo compound obtained above in the preceding step were mixed with 540 ml of 96° alcohol and 268 ml of cyclohexene, after which 30 g of palladium-on-charcoal at 10% by weight containing 50% water was added. The orange suspension was brought to reflux. After 30 minutes the decoloration was complete and the mixture was filtered while hot through a sinter funnel. The filtrate thus obtained was cooled to 0° C. The precipitate was recovered and then filtered, washed with alcohol, with isopropyl ether, with petroleum ether and then dried. 72 g of product were obtained. This product was recrystallized from 96° ethanol and gave white crystals of 4-amino-2,2-dimethyl-2,3-dihydrobenzofuran-7-ol whose melting point was 194° C. The elemental analysis for $C_{10}H_{13}NO_2$ was:

| % | C | H | N | Cl |
|---|---|---|---|---|
| Calculated | 67.02 | 7.31 | 7.82 | 17.85 |
| Found | 67.24 | 7.42 | 7.92 | 17.72 |

APPLICATION EXAMPLES

Examples 2 to 5 of Dyeing in Alkaline Medium

The dye compositions below, in accordance with the invention, were prepared (contents in grams):

| COMPOSITION | 2 | 3 | 4 | 5 |
|---|---|---|---|---|
| 4-amino-2,2-dimethyl-2,3-dihydrobenzofuran-7-ol | 0.537 | 0.537 | — | — |
| 7-amino-3H-benzimidazol-4-ol hydrochloride | — | — | 0.627 | 0.637 |
| 3-aminophenol | 0.327 | — | 0.327 | — |
| 5-N-(β-hydroxyethyl)-amino-2-methylphenol | — | 0.501 | — | 0.501 |
| Common dye support | (*) | (*) | (*) | (*) |
| Demineralized water qs | 100 g | 100 g | 100 g | 100 g |

| (*) common dye support: | |
|---|---|
| Oleyl alcohol polyglycerolated with 2 mol of glycerol | 4.0 g |
| Oleyl alcohol polyglycerolated with 4 mol of glycerol, containing 78% active material (A.M.) | 5.69 g A.M. |
| Oleic acid | 3.0 g |
| Oleylamine containing 2 mol of ethylene oxide, sold under the trade name ETHOMEEN O12 by the company Akzo | 7.0 g |
| Diethylaminopropyl laurylamino-succinamate, sodium salt, containing 55% A.M. | 3.0 g A.M. |
| Oleyl alcohol | 5.0 g |
| Oleic acid diethanolamide | 12.0 g |
| Propylene glycol | 3.5 g |
| Ethyl alcohol | 7.0 g |

-continued

| | |
|---|---|
| Dipropylene glycol | 0.5 g |
| Propylene glycol monomethyl ether | 9.0 g |
| Sodium metabisulphite as an aqueous solution containing 35% A.M. | 0.455 g A.M. |
| Ammonium acetate | 0.8 g |
| Antioxidant, sequestering agent | q.s. |
| Fragrance, preserving agent | q.s. |
| Aqueous ammonia containing 20% $NH_3$ | 10 g |

Each dye composition 2 to 5 was mixed, at the time of use, with an equal amount by weight of an oxidizing composition comprising 20-volumes aqueous hydrogen peroxide solution (6% by weight).

Each resulting composition was applied for 30 minutes to locks of natural grey hair containing 90% white hairs or to permanent-waved hair. The locks of hair were then rinsed, washed with a standard shampoo and then dried.

The locks of hair were dyed in the shades given in the table below:

| EXAMPLE | SHADE ON NATURAL HAIR | SHADE ON PERMANENT-WAVED HAIR |
|---|---|---|
| 2 | slightly golden | slightly golden |
| 3 | iridescent pale beige | iridescent pale copper |
| 4 | very pale ash | natural grey |
| 5 | matte ash | matte grey |

We claim:

1. A composition for the oxidation dyeing of keratin fibers comprising,
   a) at least one oxidation base chosen from para-aminophenols of formula (I) and acid-addition salts thereof:

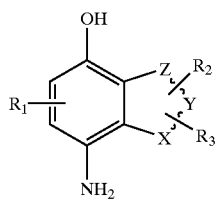

in which:
   $R_1$ is chosen from a hydrogen atom, linear and branched $C_1$–$C_4$ alkyl radicals, and $C_1$–$C_4$ trifluoroalkyl radicals;
   $R_2$ and $R_3$ independently are chosen from a hydrogen atom, $C_1$–$C_4$ alkyl radicals, and $C_1$–$C_4$ monohydroxyalkyl radicals; and
   X, Y and Z independently represent a carbon, nitrogen, oxygen or sulphur atom, wherein the bonds XY and YZ are independently single or double bonds; and
   b) a medium suitable for dyeing keratin fibers.

2. A composition according to claim 1, wherein said keratin fibers are human keratin fibers.

3. A composition according to claim 2, wherein said human keratin fibers are hair.

4. A composition according to claim 1, wherein said at least one oxidation base is present in an amount ranging from 0.0005 to 12% by weight relative to the total weight of the composition.

5. A composition according to claim 4, wherein said at least one oxidation base is present in an amount ranging from 0.005 to 6% by weight relative to the total weight of the composition.

6. A composition according to claim 1, wherein said medium suitable for dyeing comprises water or a mixture of water and at least one organic solvent.

7. A composition according to claim 6, wherein said at least one organic solvent is chosen from $C_1$–$C_4$, lower alkanols, glycerols, glycols, glycol ethers, and aromatic alcohols.

8. A composition according to claim 6, wherein said at least one organic solvent is present in an amount ranging from 1 to 40% by weight relative to the total weight of said composition.

9. A composition according to claim 1, wherein said composition has a pH ranging from 3 to 12.

10. A composition according to claim 9, wherein said composition has a pH ranging from 5 to 11.

11. A composition according to claim 1, wherein said composition further comprises at least one additional oxidation base other than said at least one oxidation base.

12. A composition according to claim 11, wherein said at least one additional oxidation base is chosen from para-phenylenediamine, bis(phenyl)-alkylenediamines, para-aminophenol, ortho-aminophenol, and heterocyclic bases.

13. A composition according to claim 11, wherein said at least one additional oxidation base is present in an amount ranging from 0.0005 to 12% by weight relative to the total weight of the composition.

14. A composition according to claim 13, wherein said at least one additional oxidation base is present in an amount ranging from 0.005 to 6% by weight relative to the total weight of the composition.

15. A composition according to claim 1, wherein said composition further comprises at least one coupler and/or at least one direct dye.

16. A composition according to claim 15, wherein said at least one coupler is chosen from meta-phenylenediamine, meta-aminophenol, metadiphenol, heterocyclic couplers, and acid-addition salts thereof.

17. A composition according to claim 15, wherein said at least one coupler is present in an amount ranging from 0.0001 to 10% by weight relative to the total weight of the composition.

18. A composition according to claim 17, wherein said at least one coupler is present in an amount ranging from 0.005 to 5% by weight relative to the total weight of the composition.

19. A composition according to claim 1, wherein said acid-addition salts are chosen from hydrochlorides, hydrobromides, sulphates, tartrates, lactates, and acetates.

20. A composition according to claim 1, wherein said composition is in the form of a liquid, cream, gel, or any form suitable for dyeing keratin fibers.

21. A process for dyeing keratin fibers comprising
   applying at least one composition for the oxidation dyeing of keratin fibers to said keratin fibers;
   developing a color at acidic, neutral or alkaline pH using at least one oxidizing agent;
   wherein said oxidizing agent is added to said at least one composition for the oxidation dyeing of keratin fibers at the time of use, or said oxidizing agent is present in an oxidizing composition applied simultaneously or sequentially in a separate manner; and
   wherein said at least one composition for the oxidation dyeing of keratin fibers comprises, in a medium suitable for dyeing, at least one oxidation base chosen from para-aminophenols of formula (I) and acid-addition salts thereof:

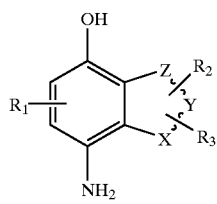

in which:
R₁, is chosen from a hydrogen atom, linear and branched $C_1$–$C_4$, alkyl radicals, and $C_1$–$C_4$, trifluoroalkyl radicals;
R₂ and R₃, independently are chosen from a hydrogen atom, $C_1$–$C_4$, alkyl radicals, and $C_1$–$C_4$ monohydroxyalkyl radicals; and
X, Y and Z independently represent a carbon, nitrogen, oxygen or sulphur atom, wherein the bonds XY and YZ are independently single or double bonds.

22. A process according to claim 21, wherein said keratin fibers are human keratin fibers.

23. A process according to claim 22, wherein said human keratin fibers are hair.

24. A process according to claim 21, further comprising, at the time of use but before said applying,
preparing a mixture of said at least one composition for the oxidation dyeing of keratin fibers and an oxidizing composition containing, in a medium suitable for dyeing keratin fibers and in an amount sufficient to develop a coloration, at least one oxidizing agent:
then applying said mixture to said keratin fibers;
leaving said mixture on said keratin fibers for a time ranging from 3 to 50 minutes;
rinsing said keratin fibers;
washing said keratin fibers with shampoo; and
rinsing and drying said keratin fibers; and
wherein said at least one composition for the oxidation dyeing of keratin fibers comprises in a medium suitable for dyeing, at least one oxidation base chosen from para-aminophenols of formula (I) and acid-addition salts thereof:

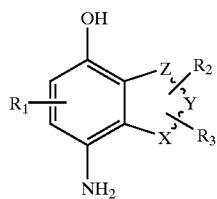

in which:
R₁, is chosen from a hydrogen atom, linear and branched $C_1$–$C_4$, alkyl radicals, and $C_1$–$C_4$, trifluoroalkyl radicals;
R₂ and R₃, independently are chosen from a hydrogen atom, $C_1$–$C_4$, alkyl radicals, and $C_1$–$C_4$ monohydroxyalkyl radicals; and
X, Y and Z independently represent a carbon, nitrogen, oxygen or sulphur atom, wherein the bonds XY and YZ are independently single or double bonds.

25. A process according to claim 24, wherein said mixture is left on said keratin fibers for a time ranging from 5 to 30 minutes.

26. A process according to claim 24, wherein said keratin fibers are human hair.

27. A process according to claim 21, wherein said at least one oxidizing agent is chosen from hydrogen peroxide, urea peroxide, alkali metal bromates, and persalts.

28. A process according to claim 27, wherein said persalts are chosen from perborates and persulphates.

29. A process according to claim 27, wherein said at least one oxidizing agent is hydrogen peroxide.

30. A multi-compartment dyeing kit comprising a first compartment containing at least one composition for the oxidation dyeing of keratin fibers, and a second compartment containing an oxidizing composition,
wherein said at least one composition for the oxidation dyeing of keratin fibers comprises, in a medium suitable for dyeing at least one oxidation base chosen from para-aminophenols of formula (I) and acid-addition salts thereof:

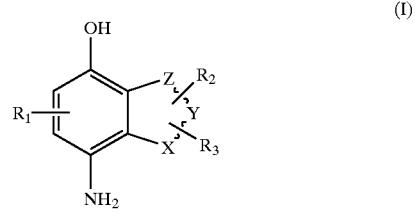

in which:
R₁, is chosen from a hydrogen atom, linear and branched $C_1$–$C_4$, alkyl radicals, and $C_1$–$C_4$, trifluoroalkyl radicals;
R₂ and R₃, independently are chosen from a hydrogen atom, $C_1$–$C_4$, alkyl radicals, and $C_1$–$C_4$, monohydroxyalkyl radicals; and
X, Y and Z independently represent a carbon, nitrogen, oxygen or sulphur atom, wherein the bonds XY and YZ are independently single or double bonds.

31. 7-amino-1-methyl-1H-indol-4-ol, or an acid-addition salt thereof.

32. A composition according to claim 1, wherein said at least one oxidation base is chosen from:
4-amino-2,2-dimethyl-2,3-dihydrobenzofuran-7-ol,
7-amino-3H-benzoimidazol-4-ol,
7-aminobenzothiophen-4-ol,
4-amino-2,3-dimethylbenzofuran-4-ol,
7-amino-2,3-dimethylbenzofuran-7-ol,
7-amino-1-propyl-5-trifluoromethyl-1H-benzoimidazol-4-ol,
7-aminobenzoisothiazol-4-ol,-7-amino-1H-benzotriazol-4-ol,
4-amino-2,3-dihydro-1H-indol-7-ol,
7-aminoindan-4-ol,
7-amino-5-methyl-2,1,3-benzothiadiazol-4-ol,
7-amino-2,1,3-benzothiadiazol-4-ol,
7-amino-1-methyl-1H-indol-4-ol,
7-amino-1-(2-hydroxyethyl)-1H-indol-4-ol, and an acid-addition salts thereof.

33. A composition according to claim 32, wherein said at least one oxidation base is chosen from:
4-amino-2,2-dimethyl-2,3-dihydrobenzofuran-7-ol,
7-amino-3H-benzolmidazol-4-ol,
7-amino-1-methyl-1H-indol-4-ol, and an acid-addition safts thereof.

34. A composition according to claim 1, wherein said at least one oxidation base is chosen from benzofurans, benzoimidazoles, benzothiophenes, benzothiazoles, benzothiadiazoles, indoles, and indans.

* * * * *

UNITED STATES PATENT AND TRADEMARK OFFICE
CERTIFICATE OF CORRECTION

PATENT NO.    : 6,673,122 B1
DATED         : January 6, 2004
INVENTOR(S)   : Jean Jacques Vandenbossche et al.

It is certified that error appears in the above-identified patent and that said Letters Patent is hereby corrected as shown below:

<u>Column 12,</u>
Lines 54-55 and 60-61, "and an acid-addition salts" should read -- and acid-addition salts --.

Signed and Sealed this

Fifteenth Day of June, 2004

JON W. DUDAS
*Acting Director of the United States Patent and Trademark Office*